US006309534B1

(12) United States Patent
Fray et al.

(10) Patent No.: US 6,309,534 B1
(45) Date of Patent: Oct. 30, 2001

(54) APPARATUS AND METHOD FOR MEASURING THE COMPOSITION OF GASES USING IONICALLY CONDUCTING ELECTROLYTES

(76) Inventors: Derek John Fray; Ramachandran Vasant Kumar, both of University of Cambridge, Department of Materials Science and Metallurgy, Pembroke Street, Cambridge CB2 3QZ (GB)

(*) Notice: Subject to any disclaimer, the term of this patent is extended or adjusted under 35 U.S.C. 154(b) by 0 days.

(21) Appl. No.: 09/446,850
(22) PCT Filed: Jul. 3, 1998
(86) PCT No.: PCT/GB98/01978
  § 371 Date: Mar. 21, 2000
  § 102(e) Date: Mar. 21, 2000
(87) PCT Pub. No.: WO99/01755
  PCT Pub. Date: Jan. 14, 1999

(30) Foreign Application Priority Data

Jul. 3, 1997 (GB) .................................... 9713953

(51) Int. Cl.[7] ......................... G01N 27/26; G01N 27/407
(52) U.S. Cl. .......................... 205/775; 204/427; 204/431; 205/784.5
(58) Field of Search .................... 204/402, 400, 204/421–429, 431, 432; 205/783.5, 784, 784.5, 785, 775

(56) References Cited

U.S. PATENT DOCUMENTS

| | | | |
|---|---|---|---|
| 2,805,191 | * | 9/1957 | Hersch . |
| 4,225,634 | * | 9/1980 | Tanaka et al. . |
| 4,661,211 | * | 4/1987 | Petty-Weeks . |
| 5,496,461 | | 3/1996 | Hotzel et al. . |
| 5,820,745 | * | 10/1998 | Van Geloven . |
| 5,935,398 | * | 8/1999 | Taniguchi et al. . |
| 6,007,697 | * | 12/1999 | Yagi et al. . |
| 6,051,123 | * | 4/2000 | Joshi et al. . |

FOREIGN PATENT DOCUMENTS

| 0520528 | 12/1992 | (EP) . |
|---|---|---|
| 0769694 | 4/1997 | (EP) . |

* cited by examiner

Primary Examiner—T. Tung
(74) Attorney, Agent, or Firm—Saliwanchik, Lloyd & Saliwanchik (57) ABSTRACT

The subject method and apparatus pertains to the accurate determination of a composition of gases, over a very wide range of compositions. The subject invention can utilize an ionic electrolyte (1), which separates gases of different compositions, a source of potential difference (2) which is applied across the ionic electrolyte, means for reversing the current, and means (3) for measuring the respective currents. The ratio of currents is a function of the ratio of the gas compositions on opposite sides of the electrolyte. By varying the applied potential, the sensitivity of the apparatus can be increased.

19 Claims, 8 Drawing Sheets

APPARATUS AND METHOD FOR MEASURING THE COMPOSITION OF GASES USING IONICALLY CONDUCTING ELECTROLYTES

FIELD OF THE INVENTION

The present invention relates to apparatus and method for measuring the composition of gases using ionically conducting electrolytes. In particular, it relates to sensors useful in the detection of gases, such as oxygen in air/fuel mixtures, extending over a range of compositions from those which are fuel-rich, containing minute quantities of oxygen, to those containing several percent of oxygen.

BACKGROUND OF THE INVENTION

The monitoring and control of gases during combustion is of increasing importance. Therefore, it is necessary to develop inexpensive, robust and reliable sensors having high sensitivity and selectivity. The sensors can be used to control the combustion process, and to detect when inefficient combustion is occurring, when toxic gases are being released and when the combustion unit requires tuning.

Two types of solid state sensor have been used for the determination of the oxygen content of gases. The electrolyte that is usually used is stabilised zirconia which comprises a solid solution of zirconium oxide and calcium oxide, magnesium oxide or yttrium oxide. In one mode, the potential is measured across the electrolyte when the gas to be measured is on one side of the electrolyte and a reference gas, of known oxygen partial pressure, is on the other side of the electrolyte. In another mode, the electrolyte is separated from gas by a pinhole or a porous layer, a potential is applied and the current measured.

In the potentiometric mode, the potential is measured across the electrolyte and the gas composition on either side of the electrolyte is given by the well-known Nernst equation:

$$-ZEF = RT \ln p'_{x2}/p''_{x2} \qquad (1)$$

where Z is the charge carried, E is the measured potential, F is Faraday's constant, R is the gas constant, and $P'_{x2}$ and $P''_{x2}$ are the pressures of gas on either side of the electrolyte. It can be appreciated that, if the potential is measured and the gas composition is known on one side of the electrolyte, the gas composition on the other side of the electrolyte can be determined. This approach has been used to great effect in controlling the internal combustion engine and burners, around the stoichiometric ratio, where the gas goes from highly reducing to highly oxidising over a small range of air/fuel ratio. Under these conditions, the oxygen pressure changes dramatically and a large potential change results.

However, for some engines and many combustion systems, it is preferable to operate in a region where excess air is used and the residual gases contain free oxygen. In such a lean-burn system, unlike the circumstances occurring around the stoichiometric region, there is very little change in oxygen partial pressure, which results in very small changes in the Nernst potential, given by equation (1). In many cases, the predicted change in potential is less than the scatter in the reading.

In order to circumvent this problem, an amperometric sensor has been used which comprises an electrolyte plate or cup, with an electrode on each face, separated from the gas source by a pinhole or porous coating. On the application of a voltage across the electrolyte, via the electrodes, oxygen ionises to ions which pass through the electrolyte to where the ions are discharged to oxygen gas at the other electrode. The supply of oxygen to the ionising electrode is controlled by the supply of oxygen via the pinhole or the porous coating and, therefore, the measured current is dependent on the supply of oxygen.

As the concentration at the electrode surface is zero (as all the oxygen is ionised), the current is linearly dependent on the oxygen concentration in the gas external to the pinhole or the porous coating. Furthermore, the measured current is usually found to be independent of the applied potential. However, it is extremely difficult to maintain the size of the pore or the porosity to any degree of reliability. For this reason, these sensors are not widely used, and the development of lean-burn engines and combustion systems has been restricted.

SUMMARY OF THE INVENTION

If two different partial pressures of a gas are separated by an ionic conductor which conducts the ion of the gas and a potential is applied between the two electrodes attached to the surfaces of the electrolyte, a current flows. The present invention is based on the discovery that, if the magnitude of the potential is kept the same but reversed, a different current flows, and that the ratio of the currents is a function of the difference in partial pressures.

The ratio of the current in the forward ($I_{for}$) and the reverse ($I_{rev}$) direction is quantitatively related to the partial pressure of oxygen in the test gas through the following equations:

$$I_{for}/I_{rev} = (V_{appl} + emf)/(V_{appl} - emf) \qquad (2)$$

where, $$emf = 2.303[RT/4F] \log [pO_2(ref)/pO_2(test)] \qquad (3)$$

According to one aspect of the invention, apparatus for measuring the composition of oxygen or any other gaseous species, includes (a) an electrolyte which conducts ions of the gaseous species and which separates two compositions containing the gas species to be measured;

(b) means for applying a potential difference across the electrolyte;

(c) means for reversing the applied voltage; and (d) means for determining the ratio of the respective currents.

The present invention provides a single sensor which can operate at high sensitivity over the whole range of partial pressures of a gas. Compared to the amperometric sensor, no pinhole or porous layer is required, which makes the apparatus considerably simpler. Further, the measured currents and current ratio are always a function of the applied potential which is unlike the amperometric sensors where the current is independent of the applied voltage. Depending on the magnitude of the potential, the present invention makes it possible to measure the oxygen partial pressure accurately over the whole range. This makes the sensing apparatus far more flexible than either the potentiometric or amperometric sensor.

DESCRIPTION OF THE DRAWINGS

The invention will be described by way of example only with reference to the accompanying drawings, in which.

DESCRIPTION OF THE INVENTION

The electrolyte used in the invention may be solid or liquid. The preferred electrolyte is solid, in the shape of a tube or a pellet, sealed into a tube of silica. A refractory or planar arrangement may also be used. The pellet may be of the order of 5 mm in diameter and the tube may 5 mm in diameter and 30 mm in length. It will be appreciated that the dimensions of the pellet and tube are not critical. If the electrolyte is liquid, it may be necessary to restrain it in a porous structure.

Electrical leads may be placed on the two surfaces of the electrolyte. A catalytic coating may be applied.

In use, a potential is applied and the current is measured, then the potential is reversed and the current is remeasured. The ratio of the currents is then taken.

It is preferred that the composition of the gas on one side of the electrolyte is kept constant. In the case of oxygen-sensing, this can be achieved by exposing the electrolyte to air or a solid state mixture of metal/metal oxide.

The sensor may be placed directly into the gas, which may be stagnant or flowing, at a temperature sufficient for the electrolyte to conduct ionically. Preferably, the temperature is in the range 400–1000° C.

The sensor can be used to determine directly the gas composition from the plot of current ratio versus composition. If the gas composition needs to be controlled, the gas composition can be varied until the current ratio, given by the sensor, is at the desired value.

By varying the applied potential so that it approaches the Nernst potential for a given set of conditions, the sensitivity of the device can be increased.

Alternatively, a potential may be applied which is equal to the Nernst potential, where it is found that the current ratio is at its maximum. The gas composition is then altered until the maximum current ratio is found; this then equates to the desired gas composition.

The apparatus of the present invention may be utilised for the detection of a wide range of gases, dependent upon the ionically-conducting electrolyte. For example, oxygen-conducting electrolytes such as zirconia stabilised with calcium oxide, magnesium oxide or yttrium oxide, will respond to oxygen. Proton-conducting oxides such as strontium cerate, and calcium zirconate doped with trivalent ions, will respond to hydrogen. Chloride-based electrolytes will respond to chlorine.

Surprisingly, it is found that the sensor combines both the advantages of the potentiometric sensors and amperometric sensors into a single sensor which can be used over a very wide range of gas concentrations. Furthermore, there is no requirement for a porous coating or pinhole in order to obtain a linear response at the higher concentrations. It can be appreciated that, by taking the ratio of the currents, the measurement is independent of the conductivity of the electrolyte, its thickness and the area of its surface exposed to the gas. This makes it considerably simpler than existing sensors.

In addition, the response time of the sensors is limited only by the applied frequency, the exact limit of which has yet to be established. Faster responses can be obtained at higher operating temperatures, which would permit operations at higher frequencies. It was observed that accurate measurements of gas compositions could be made at rates much faster than that associated with prior art sensors.

Figure 1:
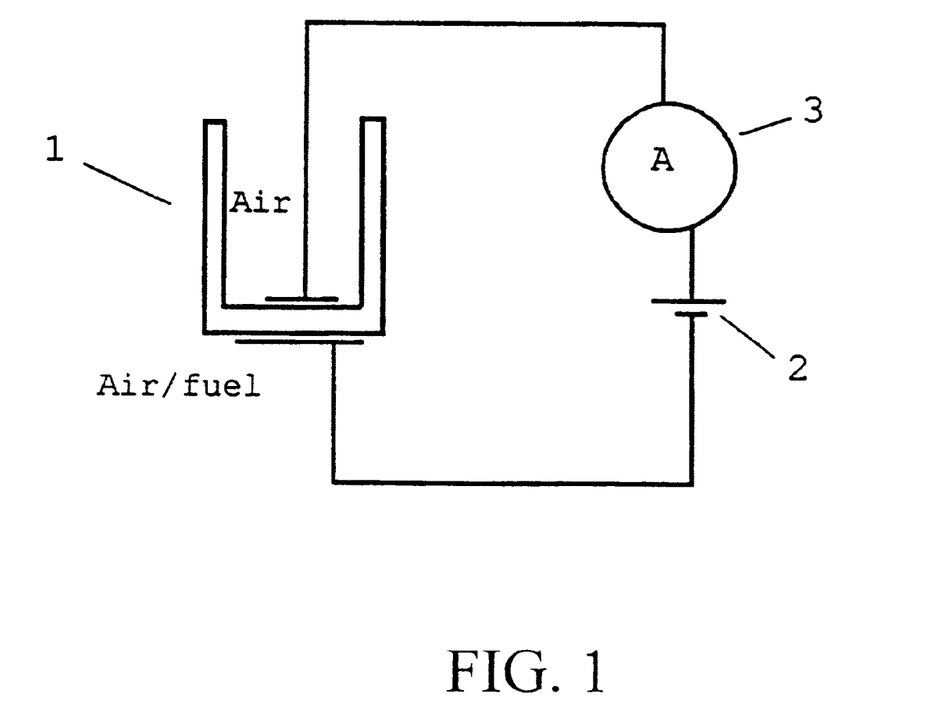
FIG. 1 is a schematic illustration of an embodiment of apparatus of the invention.

FIG. 1 shows a sensor system comprising an electrolyte 1 in the form of a container. Opposite faces of the electrolyte 1 are connected via a voltage source 2 and an ammeter 3. In use, the applied potential difference may be reversed manually; it will be appreciated that this can be achieved by automated means (not shown).

The following Example illustrates the invention.

EXAMPLE

Figure 2:
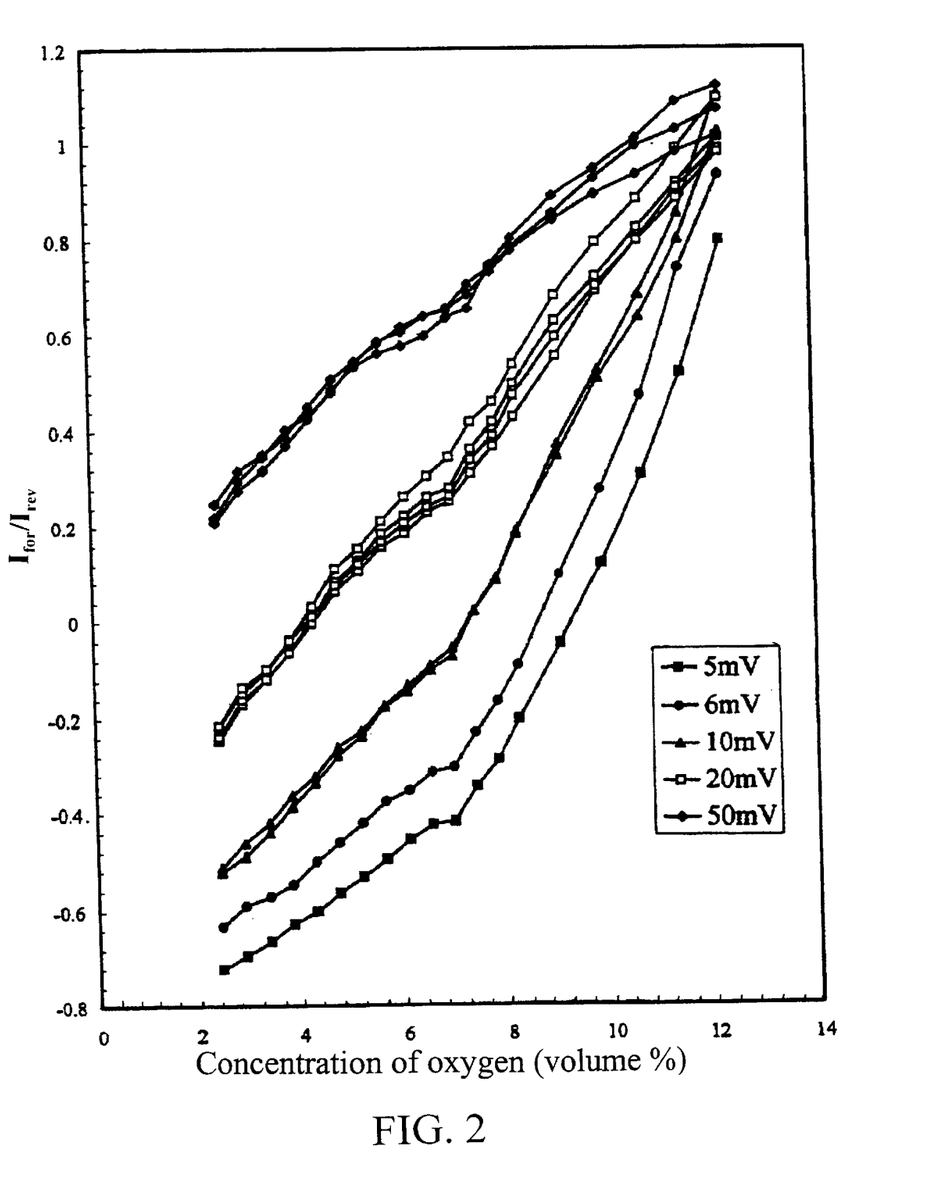
FIG. 2 is a graph of current ratio as a function of oxygen content, with air as the reference gas and different applied voltages.
Figure 3:
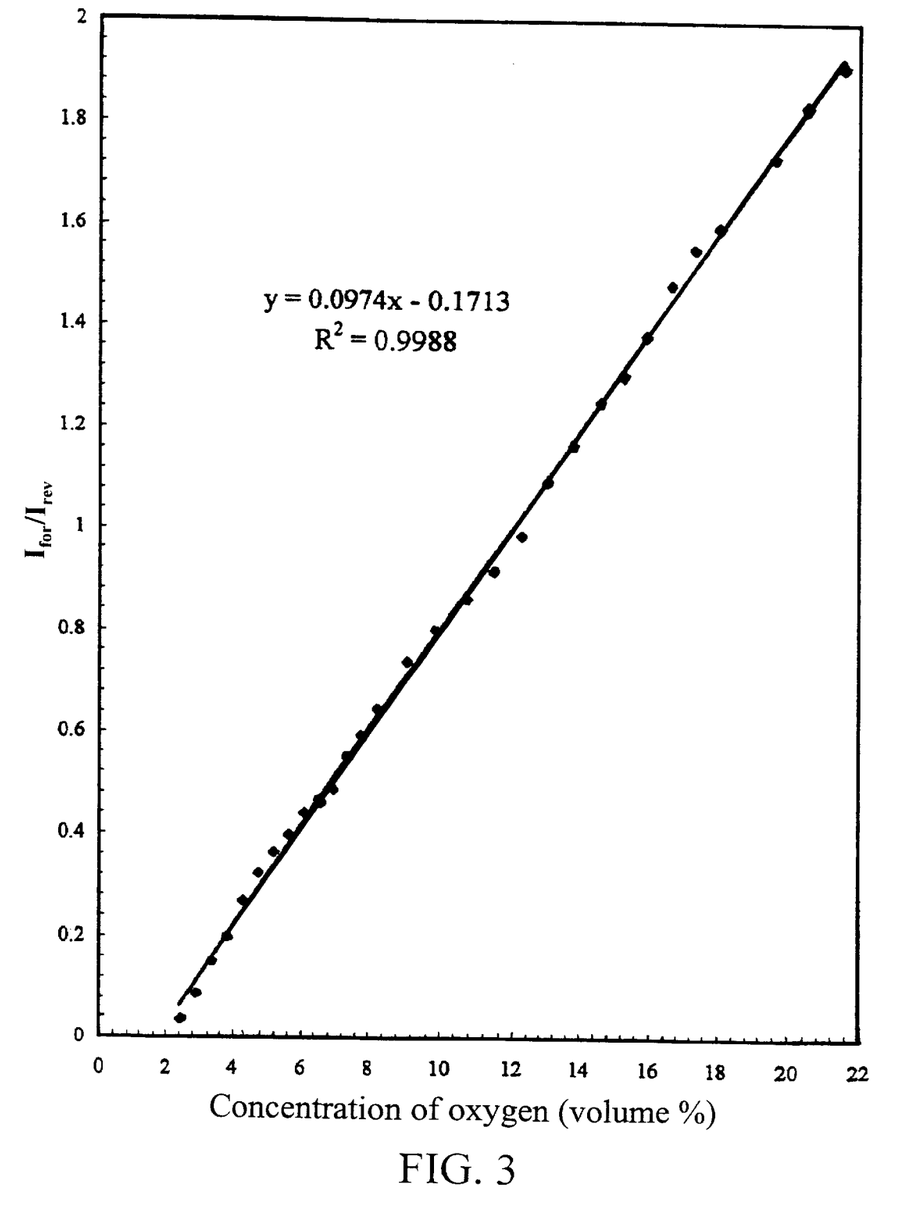
FIG. 3 is a graph of current ratio as a function of oxygen content, with air as the reference gas and an applied voltage of 35 mV.

A yttrium-stabilised zirconia sensor (Standard "lambda" Bosch Sensor), in the form of a tube, was used to measure oxygen composition in a ($O_2$/$N_2$) sample with air as a reference at 674° C. (947 K). Various potential differences were applied in the forward and reverse directions with a frequency of 0.25–2 Hz, and the $O_2$ composition varied by altering the sample flow rate. The results are given in FIG. 2 and FIG. 3, where it is shown that the current ratio ($I_{for}/I_{rev}$) is almost linearly dependent upon oxygen concentration. At high oxygen concentrations, a linear response is more sensitive than the logarithmic dependence obtained with potentiometric methods. The small departure from linearity is not considered a problem as the main issue is that of sensitivity at the appropriate range of concentrations, and equations (2) and (3) describe the response quantitatively. Sensitivity is related to the rate of change of the signal with respect to the oxygen concentration, given by a $(I_{for}/I_{rev})$/$dpO_2$ is constant. In many applications, higher sensitivity rather than linearity may be desirable.

Figure 4:
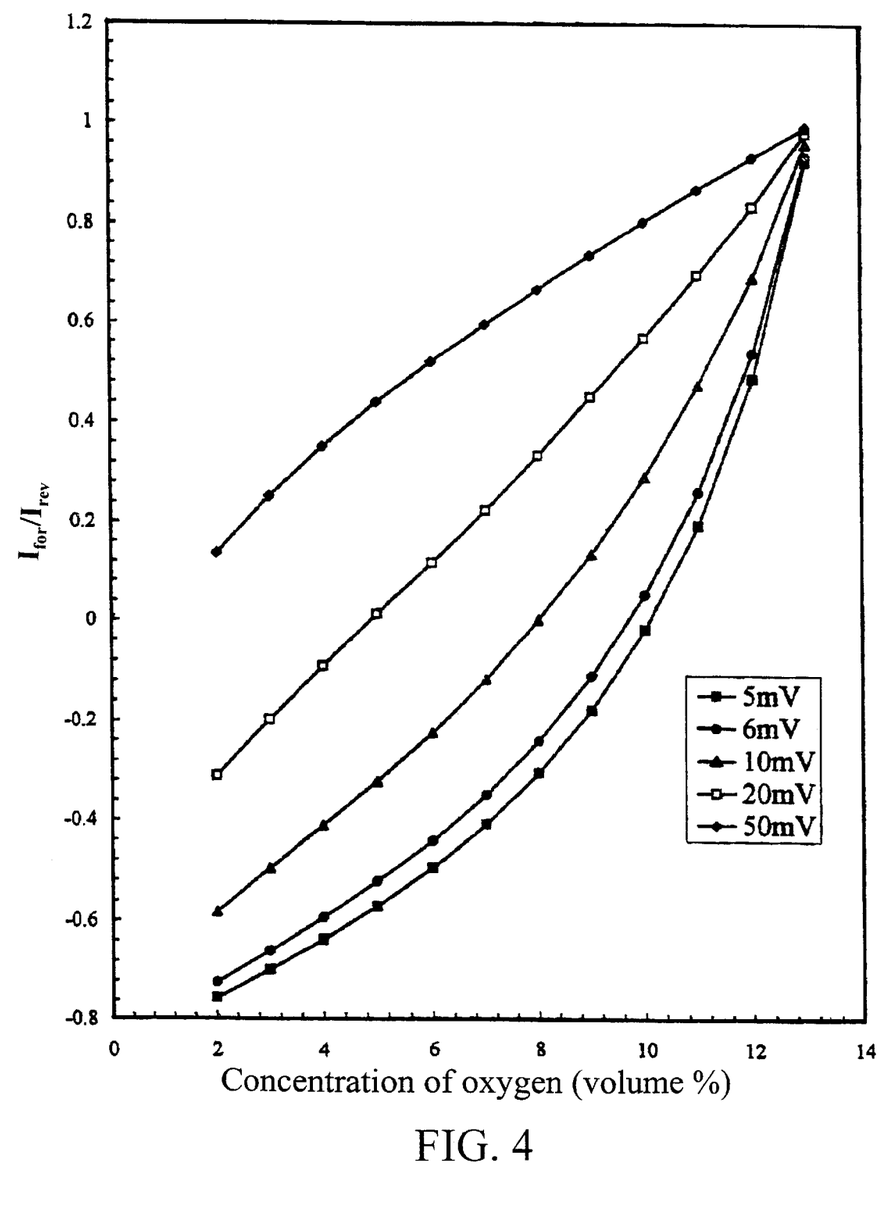
FIG. 4 is a graph of calculated values of current ratio as a function of oxygen content at different applied voltages.

The sensitivity factor at any given oxygen concentration is a function of the applied potential, as shown in FIG. 4 for oxygen in the 2–14%, concentration range. Lower applied potentials (e.g. 5 mV) have resulted in greater sensitivity, while higher values (e.g. 50 mV) have produced a linear response.

The experimental data accurately reproduces calculated values and it is therefore possible to calculate the theoretical values of the sensitivity factor, $d(I_{for}/I_{rev}/dpO_2)$, in any given oxygen concentration range for different values of applied potentials, in order to select the optimum operating conditions. Some typical calculated values are shown in Table 1, where (I) is the current value obtained at the forward potential and (Io) is the current value obtained at the reverse potential. Oxygen concentration (volume %)=$PO_2$ (% atm). It can be seen that, for the range covering 0.02 to 0.5 $PO_2$ (atm), considerable sensitivity, as represented by $dI/I_o/dpO_2$, is obtained. For example, at V=20 mV, the linear range is 0.05 to 0.09; at V=40 mV, it is 0.05 to 0.21; at very low applied voltages (10 mV), there is no linear region, although the sensitivity is high. This applied potential (10 mV) is close to the Nernst potential of zero mV for this system. It can be seen that, by applying an applied potential close to the Nernst value, a very large current ratio is obtained. This shows that the sensor may be used for control at a predetermined value. The desired potential for a given gas composition is applied and the gas composition changed until the maximum current ratio is obtained which would pertain to the given gas composition.

TABLE I

Sensitivity of Current Ratio vs Oxygen Pressure
(Temperature = 947 K.; Reference = Air)

| $pO_2$ (atm) | $\frac{dI/Io}{dpO_2}$ (V = 20 mV) $atm^{-1}$ | $\frac{dI/Io}{dpO_2}$ (V = 40 mV) $atm^{-1}$ | $\frac{dI/Io}{dpO_2}$ (V = 10 mV) $atm^{-1}$ |
| --- | --- | --- | --- |
| 0.01 | 35 | 43.5 | 23.7 |
| 0.02 | 27 | 30 | 13 |
| 0.03 | 25 | 25 | 19.6 |
| 0.04 | 23.5 | 22.5 | 19.5 |
| 0.05 | 23.4 | 20.8 | 20.8 |
| 0.06 | 23.7 | 19.7 | 22.5 |
| 0.07 | 24.3 | 18.9 | 24.8 |
| 0.08 | 25.18 | 18.3 | 27.82 |
| 0.09 | 26.36 | 18 | 31.3 |
| 0.1 | 27.8 | 17.8 | 36.7 |
| 0.13 | 35 | 17.5 | 72.3 |
| 0.21 | 10.6 | 18.6 | 5526 |
| 0.5 | 79 | 29.7 | 1.95 |

Further results are shown in FIGS. 5 to 8.

Figure 5:
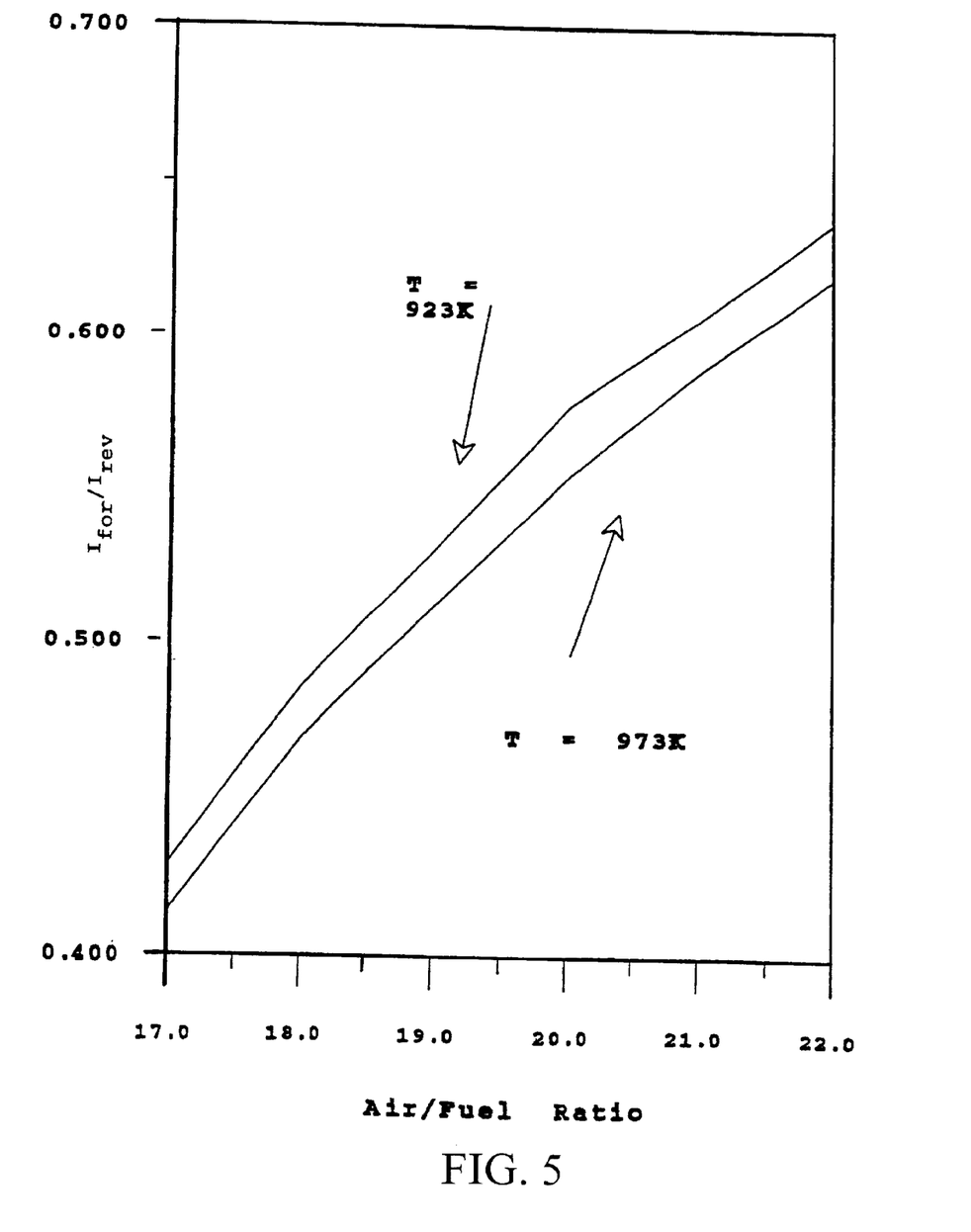
FIG. 5 is a graph of the effect of temperature on a sensor.

FIG. 5 shows that the current ratio is relatively independent of the temperature. Air is the reference gas. This can be contrasted with the potentiometric gas sensor which is linearly dependent on the temperature.

Figure 6:
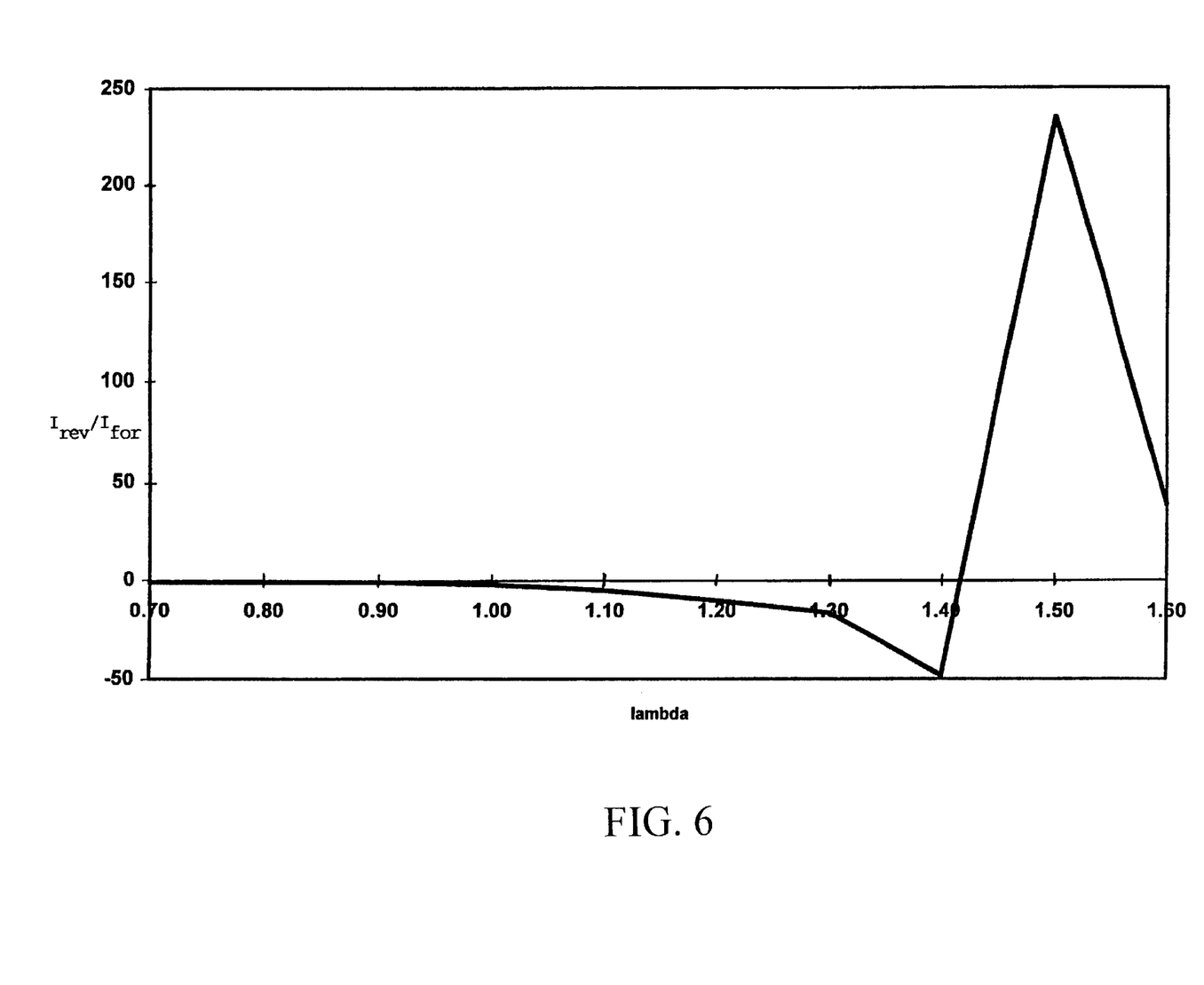
FIG. 6 is a graph of the measurement of the inverse current ratio using an applied voltage approximate to the Nernst potential.

FIG. 6 shows that, if the applied potential is very similar to the Nernst potential, the inverse current ratio effectively goes to infinity at the gas composition defined by the Nernst potential. Air is the reference gas.

Figure 7:
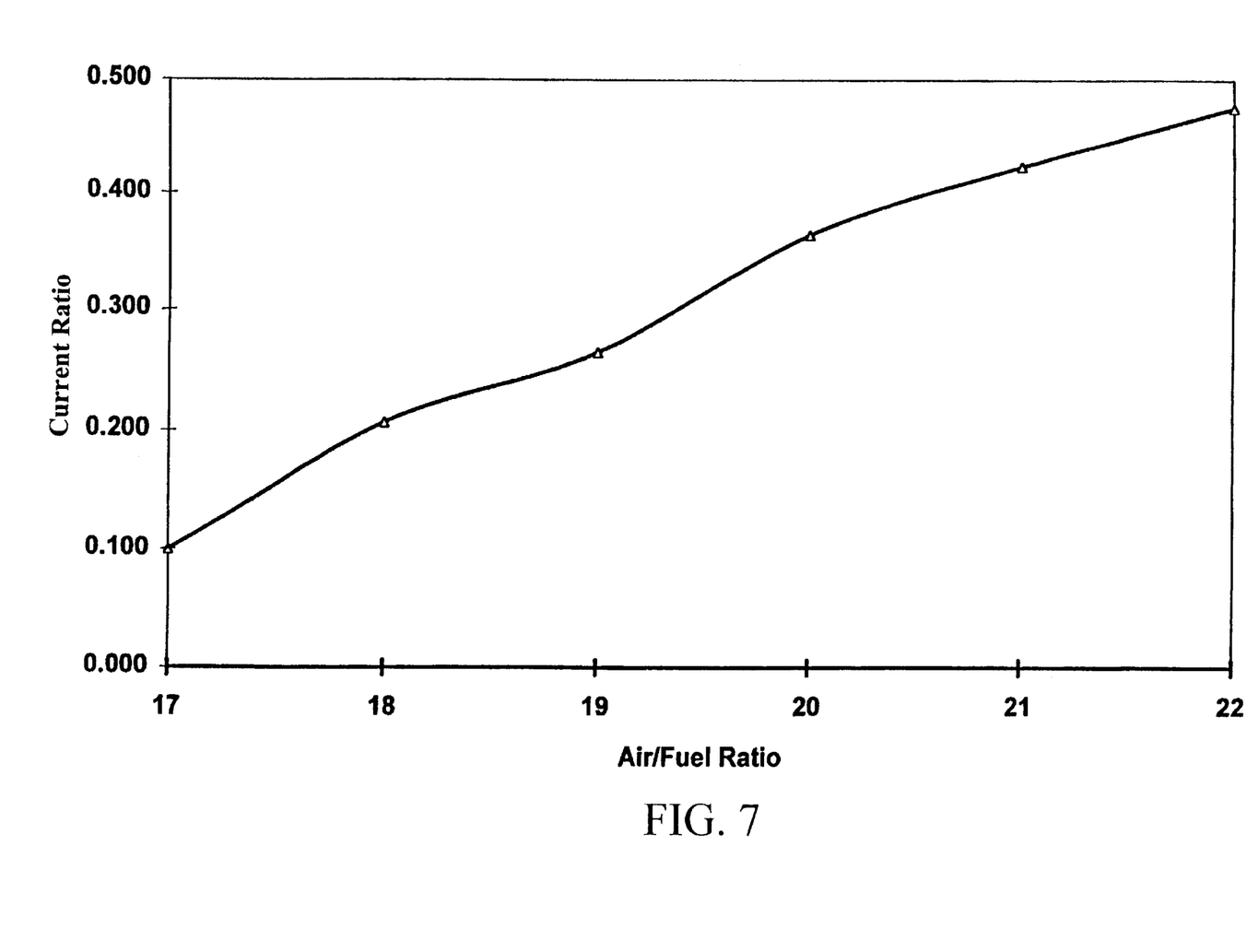
FIG. 7 is a graph of the current ratio as a function of the air/fuel ratio in a lean-burn combustion system.

For any given fuel being combusted in air, the partial pressure or concentration of oxygen can be calculated for any given air/fuel ratio. FIG. 7 shows the current ratio can be used to calculate oxygen concentration (air/fuel ratio) in a lean-burn combustion system.

Figure 8:
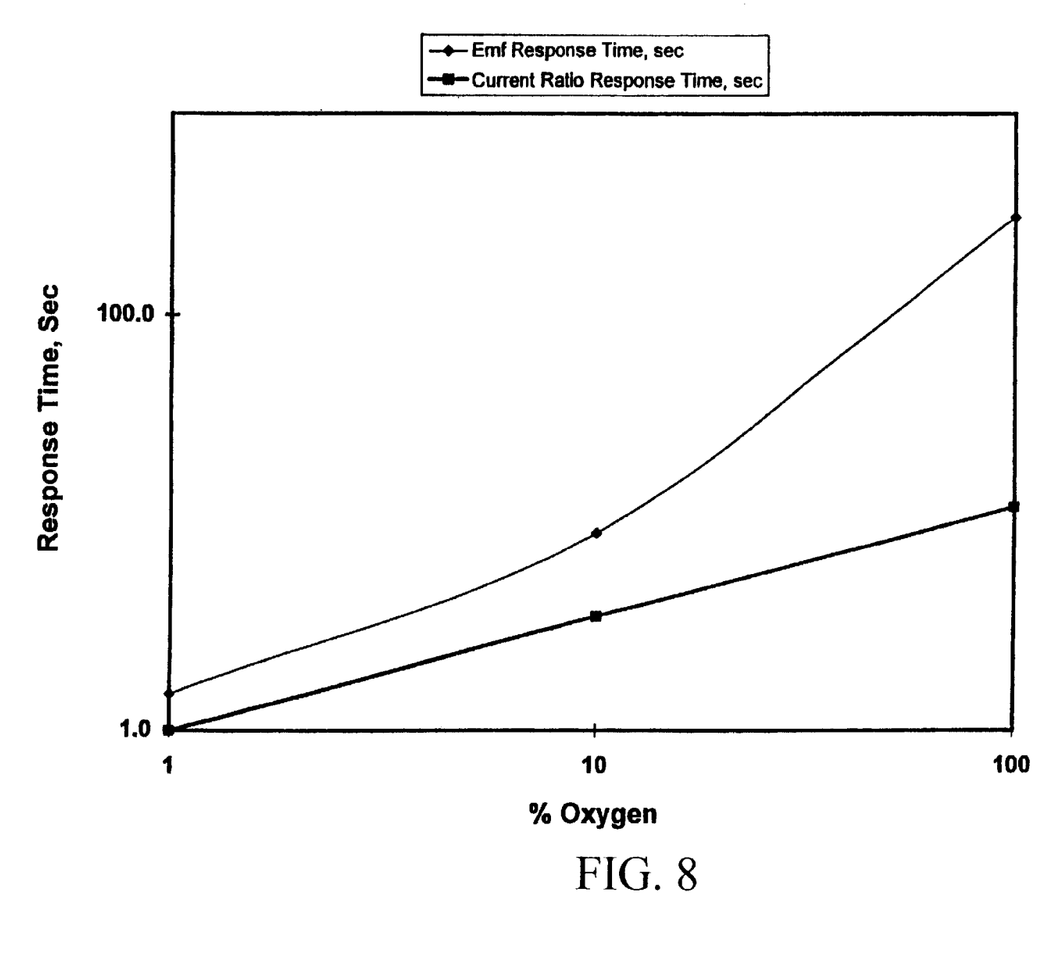
FIG. 8 is a graph of the response time as a function of oxygen content using the present invention and the potentiometric emf method.

FIG. 8 shows that the response time is reduced using the present invention compared to the potentiometric emf method.

What is claimed is:

1. An apparatus for measuring the composition of a gas, comprising an electrolyte separating a gas from a known composition of gas; means for applying a potential difference across the electrolyte to generate a first current; means for reversing the potential difference across the electrolyte to generate a second current; means for measuring the first current associated with the potential difference across the electrolyte; means for measuring the second current associated with the reversed potential difference across the electrolyte; and means for determining the ratio of the first current and the second current.

2. The apparatus according to claim 1, wherein the electrolyte is solid.

3. The apparatus according to claim 1, wherein the electrolyte is liquid.

4. The apparatus according to claim 3, wherein the liquid electrolyte is contained within a ceramic structure.

5. The apparatus according to claim 1, wherein the electrolyte conducts oxygen ions.

6. The apparatus according to claim 1, wherein the electrolyte is zirconia stabilized with calcium oxide, magnesium oxide or yttrium oxide.

7. The apparatus according to any of claim 1, wherein the electrolyte conducts hydrogen ions.

8. The apparatus according to claim 7, wherein the electrolyte is a perovskite.

9. The apparatus according to claim 8, wherein the electrolyte is strontium cerate or calcium zirconate.

10. The apparatus according to claim 7, wherein the electrolyte is strontium cerate or calcium zirconate.

11. A method for measuring the composition of a gas, comprising separating a gas from a known composition of gas with an electrolyte, applying a potential difference across the electrolyte to generate a first current measuring the first current associated with the potential difference across the electrolyte, reversing the potential difference across the electrolyte to generate a second current, measuring the second current associated with the reversed potential difference across the electrolyte, and determining the ratio of the first current and second current.

12. The method according to claim 11, wherein the magnitude of the applied potential is given by the Nernst equation for the gas with respect to the known composition of gas.

13. The method according to claim 12, wherein the gas composition on one side of the electrolyte is maintained at one concentration.

14. The method according to claim 12, wherein the gas of known composition is air.

15. The method according to claim 11, wherein the gas composition on one side of the electrolyte is maintained at one concentration.

16. The method according to claim 15, wherein the gas of known composition is air.

17. A method according to claim 11, wherein the gas of known composition is air.

18. The method according to claim 11, wherein the electrolyte is solid.

19. The method according to claim 11, wherein the electrolyte is liquid.

* * * * *

UNITED STATES PATENT AND TRADEMARK OFFICE
CERTIFICATE OF CORRECTION

PATENT NO. : 6,309,534 B1
DATED : October 30, 2001
INVENTOR(S) : Derek John Fray, Ramachandran Vasant Kumar It is certified that error appears in the above-identified patent and that said Letters Patent is hereby corrected as shown below:

<u>Column 6, claim 7,</u>
Line 16, "according to any of claim 1," should read -- according to claim 1, --.

<u>Column 6, claim 11,</u>
Line 27, "first current measuring" should read -- first current, measuring --.

Signed and Sealed this

Ninth Day of April, 2002

Attest:

JAMES E. ROGAN
Attesting Officer
Director of the United States Patent and Trademark Office